(12) United States Patent
Hancock et al.

(10) Patent No.: US 12,274,495 B2
(45) Date of Patent: Apr. 15, 2025

(54) ELECTROSURGICAL SYSTEM

(71) Applicant: Creo Medical Limited, Chepstow (GB)

(72) Inventors: Christopher Hancock, Chepstow (GB); Shaun Preston, Chepstow (GB); George Ullrich, Bangor Gwynedd (GB); David Webb, Bangor Gwynedd (GB)

(73) Assignee: Creo Medical Limited, Chepstow (GB)

( * ) Notice: Subject to any disclaimer, the term of this patent is extended or adjusted under 35 U.S.C. 154(b) by 651 days.

(21) Appl. No.: 17/607,633

(22) PCT Filed: Apr. 28, 2020

(86) PCT No.: PCT/EP2020/061763
§ 371 (c)(1),
(2) Date: Oct. 29, 2021

(87) PCT Pub. No.: WO2020/221750
PCT Pub. Date: Nov. 5, 2020

(65) Prior Publication Data
US 2022/0211434 A1 Jul. 7, 2022

(30) Foreign Application Priority Data
Apr. 30, 2019 (GB) .................................... 1906009

(51) Int. Cl.
*A61B 18/18* (2006.01)
*A61B 18/00* (2006.01)

(52) U.S. Cl.
CPC ...... *A61B 18/1815* (2013.01); *A61B 2018/00077* (2013.01); *A61B 2018/00083* (2013.01);
(Continued)

(58) Field of Classification Search
CPC ...... A61B 18/1815; A61B 2018/00178; A61B 2018/00529; A61B 2018/00541;
(Continued)

(56) References Cited

U.S. PATENT DOCUMENTS

2001/0039416 A1* 11/2001 Moorman .......... A61B 10/0275
607/101
2004/0243004 A1 12/2004 Carr
(Continued)

FOREIGN PATENT DOCUMENTS

| CN | 1346248 A | 4/2002 |
|---|---|---|
| CN | 108495596 A | 9/2018 |

(Continued)

OTHER PUBLICATIONS

Search Report dated Oct. 25, 2019 in connection with GB Application No. 1906009.4.
(Continued)

Primary Examiner — Linda C Dvorak
Assistant Examiner — Abigail Bock
(74) Attorney, Agent, or Firm — Wolf, Greenfield & Sacks, P.C.

(57) ABSTRACT

Various embodiments provide an electrosurgical system for treating biological tissue. The system comprises: an electrosurgical generator configured to supply pulsed microwave energy; and an electrosurgical instrument. The electrosurgical instrument comprises a flexible coaxial cable arranged to convey the pulsed microwave energy; and a radiating tip portion connected at a distal end of the coaxial cable and configured to receive the pulsed microwave energy. The radiating tip portion has a maximum outer diameter that is 1.0 mm or less, and wherein the maximum outer diameter of the radiating tip portion is smaller than an outer diameter of the coaxial cable. Also, the radiating tip
(Continued)

portion comprises: a proximal coaxial transmission line for conveying the pulsed microwave energy; and a distal needle tip mounted at a distal end of the proximal coaxial transmission line, the distal needle tip being arranged to deliver the pulsed microwave energy into biological tissue.

11 Claims, 7 Drawing Sheets

(52) U.S. Cl.
CPC ............... *A61B 2018/00178* (2013.01); *A61B 2018/00529* (2013.01); *A61B 2018/00541* (2013.01); *A61B 2018/00577* (2013.01); *A61B 2018/00761* (2013.01); *A61B 2018/1823* (2013.01); *A61B 2018/1861* (2013.01); *A61B 2018/1869* (2013.01)

(58) Field of Classification Search
CPC ........... A61B 2018/00577; A61B 2018/00761; A61B 2018/1823; A61B 2018/1861; A61B 2018/1869
See application file for complete search history.

(56) References Cited

U.S. PATENT DOCUMENTS

| | | |
|---|---|---|
| 2006/0293651 A1 | 12/2006 | Cronin |
| 2009/0131926 A1 | 5/2009 | Rusin et al. |
| 2010/0137857 A1* | 6/2010 | Shroff ............... A61B 18/1815 606/33 |
| 2011/0077632 A1 | 3/2011 | Rossetto |
| 2012/0041433 A1 | 2/2012 | Prakash et al. |
| 2012/0259326 A1 | 10/2012 | Brannan et al. |
| 2015/0320481 A1* | 11/2015 | Cosman, Jr. ............ A61B 34/10 606/35 |
| 2016/0038232 A1 | 2/2016 | Brannan et al. |
| 2017/0118806 A1 | 4/2017 | Chu et al. |
| 2018/0036081 A1 | 2/2018 | Dickhans et al. |
| 2019/0069951 A1* | 3/2019 | Hancock ............. A61B 18/1492 |

FOREIGN PATENT DOCUMENTS

| | | |
|---|---|---|
| GB | 2569812 A | 7/2019 |
| WO | WO 2018/202758 A1 | 11/2018 |

OTHER PUBLICATIONS

International Search Report and Written Opinion mailed Jun. 22, 2020 in connection with International Application No. PCT/EP2020/061763.
Chinese Office Action dated Nov. 24, 2023, in connection with Chinese Application No. 202080032486.0.
GB 1906009.4, Oct. 25, 2019, Search Report.
PCT/EP2020/061763, Jun. 22, 2020, International Search Report and Written Opinion.

* cited by examiner

ELECTROSURGICAL SYSTEM

CROSS REFERENCE TO RELATED APPLICATIONS

This Application is a national stage filing under 35 U.S.C. 371 of International Patent Application Serial No. PCT/EP2020/061763, filed Apr. 28, 2020, entitled "ELECTROSURGICAL SYSTEM". Foreign priority benefits are claimed under 35 U.S.C. § 119(a)-(d) or 35 U.S.C. § 365(b) of British application number 1906009.4, filed Apr. 30, 2019. The entire contents of these applications are incorporated herein by reference in their entirety.

FIELD OF THE INVENTION

The invention relates to an electrosurgical system for delivering electromagnetic energy to biological tissue in order to ablate target tissue. The electrosurgical system includes an electrosurgical generator for supplying microwave energy, and an electrosurgical instrument arranged to receive the microwave energy and deliver it to target tissue. The electrosurgical instrument may be arranged to ablate tissue, such as a tumour, cyst or other lesion. The system may be particularly suited for treatment of tissue in the pancreas, the lung, or the liver.

BACKGROUND TO THE INVENTION

Electromagnetic (EM) energy, and in particular microwave and radiofrequency (RF) energy, has been found to be useful in electrosurgical operations, for its ability to cut, coagulate, and ablate body tissue. Typically, apparatus for delivering EM energy to body tissue includes a generator comprising a source of EM energy, and an electrosurgical instrument connected to the generator, for delivering the energy to tissue. Conventional electrosurgical instruments are often designed to be inserted percutaneously into the patient's body. However, it can be difficult to locate the instrument percutaneously in the body, for example if the target site is in a moving lung or a thin walled section of the gastrointestinal (GI) tract. Other electrosurgical instruments can be delivered to a target site by a surgical scoping device (e.g. an endoscope) which can be run through channels in the body such as airways or the lumen of the oesophagus or colon. This allows for minimally invasive treatments, which can reduce the mortality rate of patients and reduce intra-operative and postoperative complication rates.

Tissue ablation using microwave EM energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating.

This principle is harnessed in microwave ablation therapies, where water molecules in target tissue are rapidly heated by application of a localised electromagnetic field at microwave frequencies, resulting in tissue coagulation and cell death. It is known to use microwave emitting probes to treat various conditions in the lungs and other organs. For example, in the lungs, microwave radiation can be used to treat asthma and ablate tumours or lesions.

SUMMARY OF THE INVENTION

At its most general, the invention provides an electrosurgical system which is arranged to deliver pulsed microwave energy to biological tissue via a small-diameter (e.g. 1.0 mm or less) radiating tip portion. A benefit of using a small-diameter radiating tip portion is that a size of an insertion hole produced when inserting the radiating tip portion into target tissue can be minimised, which may reduce bleeding and facilitate healing. However, a drawback of using such a small-diameter radiating tip portion is that transmission of microwave energy through the radiating tip portion may cause excessive heating of the radiating tip portion. Such excessive heating may cause burns and thus damage healthy tissue. The inventors have overcome this drawback by configuring the electrosurgical system to deliver the microwave energy in a pulsed manner. By delivering the microwave energy in a pulsed manner, it is possible to avoid excessive heating of the radiating tip portion. This may enable effective treatment of target biological tissue the radiating tip portion, whilst avoiding damage to surrounding healthy tissue.

The radiating tip portion of conventional electrosurgical instruments which may be used to treat the liver typically have an outer diameter between 2-3 mm. The inventors have found that use of such electrosurgical instruments in the liver may produce excessive bleeding which can be difficult to get under control during a surgical procedure. If a surgeon is unable to get such bleeding under control during a surgical procedure, it may be necessary to remove the electrosurgical instrument and attempt to continue the procedure with other means.

In contrast, the electrosurgical system of the invention may be particularly suited to treating tissue in highly vascularised regions of the body (e.g. where there may be excessive bleeding when the tissue is pierced), as the small insertion hole produced by the radiating tip portion may avoid or reduce bleeding. Thus, the combination of a small-diameter radiating tip portion and pulsed microwave energy delivery may enable highly vascularised regions of the body to be treated with microwave energy. In particular, the inventors have found that using the small-diameter radiating tip portion of the electrosurgical system of the invention may avoid excessive bleeding when used to treat target tissue in the liver. Thus, the electrosurgical system of the invention may be particularly suited to use for treatment of tissue in the liver. Additionally, the small-diameter radiating tip portion may be beneficial where scarring may be an issue. For example, the electrosurgical instrument of the invention may enable scarring to be reduced when used to ablate tumours in the breasts.

According to the invention, there is provided an electrosurgical system for treating biological tissue, the system comprising: an electrosurgical generator configured to supply pulsed microwave energy; and an electrosurgical instrument comprising: a flexible coaxial cable arranged to convey the pulsed microwave energy; and a radiating tip portion connected at a distal end of the coaxial cable and configured to receive the pulsed microwave energy, wherein the radiating tip portion has a maximum outer diameter that is 1.0 mm or less, and wherein the maximum outer diameter of the radiating tip portion is smaller than an outer diameter of the coaxial cable, the radiating tip portion comprising: a proximal coaxial transmission line for conveying the pulsed microwave energy; and a distal needle tip mounted at a distal end of the proximal coaxial transmission line, the distal needle tip being arranged to deliver the pulsed microwave energy into biological tissue.

The inventors have found that, by making a maximum outer diameter of the radiating tip portion 1.0 mm or less, bleeding may be significantly reduced or avoided when the radiating tip portion is inserted into target tissue. As discussed above, the use of pulsed microwave energy may ensure that excessive heat is not generated in the radiating tip portion when the microwave energy is delivered to the radiating tip portion. In contrast to delivering the microwave energy as a continuous wave which may cause the radiating tip portion to heat up rapidly, pulsed microwave energy may facilitate maintaining the radiating tip portion at an acceptable temperature. Pulsed microwave energy delivery may also enable the total amount of time over which microwave energy is delivered to the radiating tip portion to be reduced, e.g. by delivering short high power pulses. In this manner, the electrosurgical system may be used to effectively treat (e.g. ablate) target tissue whilst avoiding damage to nearby healthy tissue.

The electrosurgical generator may be any suitable generator for controllably supplying microwave energy. A suitable generator for this purpose is described in WO 2012/076844, which is incorporated herein by reference. The electrosurgical generator may generate pulsed microwave energy by modulating a microwave energy source to produce a profile (or waveform) having a series of "on" periods (corresponding to the microwave pulses) separated by a series of "off" periods. Generally speaking, pulsed microwave energy may be microwave energy having a profile comprising a plurality of pulses (or bursts) of microwave energy that are separated by periods with no microwave energy. The pulsed microwave energy may be periodic, e.g. it may have periodic cycles with "on" and "off" periods.

Different pulsed microwave energy profiles may be used. For example, all of the microwave pulses may have a same duration, or they may have different durations. Similarly, the periods between pulses may all be the same, or they may vary over time. The pulses may have a predetermined power profile (i.e. power vs. time). In some cases, different pulses may have different power profiles, depending on a desired energy delivery profile.

The electrosurgical instrument may be dimensioned so that it is insertable into an instrument (or working) channel of a surgical scoping device. This may facilitate insertion of the electrosurgical instrument into the patient's body, to enable access to a treatment site.

The flexible coaxial cable may be a conventional low loss coaxial cable that is connectable at a proximal end to the electrosurgical generator, to receive the pulsed microwave energy. In some cases, the coaxial cable may be permanently connected to the electrosurgical generator. The coaxial cable may have a centre conductor separated from an outer conductor by a dielectric material. The coaxial cable may further include an outer protective sheath for insulating and protecting the cable. In some examples, the protective sheath may be made of or coated with a non-stick material to prevent tissue from sticking to it and/or facilitate insertion of the instrument into the instrument channel of a surgical scoping device. The radiating tip portion is located at the distal end of the coaxial cable, and is connected to receive the pulsed microwave energy conveyed along the coaxial cable.

The proximal coaxial transmission line may be electrically connected to the distal end of coaxial cable, to receive the pulsed microwave energy and convey it to the distal needle tip, where the pulsed microwave energy is delivered to target tissue. The materials used in the proximal coaxial transmission line may be the same or different to those used in the coaxial cable. The materials used in the proximal coaxial transmission line may be selected to provide a desired flexibility and/or impedance of the proximal coaxial transmission line. For example, a dielectric material of the proximal coaxial transmission line may be selected to improve impedance matching with target tissue.

The distal needle tip is formed at the distal end of the proximal coaxial transmission line. The distal needle tip may include an emitter structure which is arranged to receive the pulsed microwave energy from the proximal coaxial transmission line and deliver the energy into target tissue. The emitter structure may be configured to produce a desired ablation profile in target tissue. For example, the emitter structure may be a monopolar or bipolar microwave antenna for radiating microwave energy into surrounding tissue. In some cases, the emitter structure may also be capable of delivering radiofrequency energy to target tissue, separately or in combination with the pulsed microwave energy.

The distal needle tip may include a pointed distal tip, to facilitate insertion of the radiating tip portion into target tissue.

The maximum outer diameter of the radiating tip portion is 1.0 mm or less. For example, the radiating tip portion may be 19 gauge. In some examples, the maximum outer diameter may be 0.95 mm, 0.9 mm or less. The maximum outer diameter may refer to the largest outer diameter of the radiating tip portion along a length of the radiating tip portion.

The outer diameter of the radiating tip portion is smaller than the outer diameter of the coaxial cable. By using a smaller diameter radiating tip portion, the radiating tip portion may be more flexible than the coaxial cable. This may facilitate guiding the distal needle tip to a desired location, e.g. where it is necessary to guide the device around a tight bend. A benefit of using a coaxial cable with an outer diameter that is larger than that of the radiating tip portion is that heating in the coaxial cable may be reduced, as heating is generally related to the diameter of the coaxial cable.

A pulse duration of the pulsed microwave energy may be shorter than a thermal response time of the radiating tip portion. This may reduce heating of the radiating tip portion, as the radiating tip portion may not react thermally to a magnitude of the pulsed microwave energy within the time frame of the pulse duration. This may improve an efficiency with which microwave energy can be delivered to the distal needle tip, as heating effects (e.g. dissipation of microwave energy) along the length of the radiating tip portion may be reduced. This may serve to improve an overall efficiency with which microwave energy can be delivered to target tissue.

The pulse duration may correspond to a time duration of a pulse of microwave energy in the pulsed microwave energy supplied by the electrosurgical generator. The thermal response time may correspond to an amount of time taken for the radiating tip portion's temperature to react (e.g. to change by a given amount) when microwave energy at a given power level is delivered to the radiating tip portion. The radiating tip portion's thermal response time may depend on a heat capacity of the radiating tip portion, e.g. the larger the heat capacity, the greater the thermal response time. The thermal response time of the radiating tip portion may be measured experimentally, in order to determine a suitable pulse duration time.

In some embodiments, the electrosurgical generator may be configured to supply the pulsed microwave energy with a duty cycle of 25% or less. Making the duty cycle of the pulsed microwave energy 25% or less may avoid or reduce heating effects in the radiating tip portion. For example, a duty cycle of 25% or less may ensure that the microwave pulses are short enough so that the radiating tip portion does not have enough time to thermally react to the pulses. Herein, a duty cycle may refer to a fraction of a period of the pulsed microwave energy where microwave energy is supplied by the electrosurgical generator (the remainder of the period may correspond to an "off" period where no microwave energy is supplied). Thus, with a duty cycle of 25% or less, no microwave energy may be delivered for at least 75% of the period of the pulsed microwave energy. This may ensure that pauses between the pulses of microwave energy are sufficiently long, so that there is little or no accumulation of thermal effects across multiple pulses.

A pulse duration of the pulsed microwave energy may be between 10 ms and 200 ms. The inventors have found that by using a pulse duration between 10 ms and 200 ms, it may be possible to avoid or reduce heating effects in the radiating tip portion, so that the radiating tip portion may be maintained at an acceptable temperature. Combining a pulse duration between 10 ms and 200 ms with a duty cycle of 25% or less may further ensure that heating effects are avoided or reduced.

In some embodiments, the pulsed microwave energy may be delivered according to one of the following cycles:

a) 10 ms pulse duration, with 90 ms between pulses;
b) 10 ms pulse duration, with 50 ms between pulses;
c) 10 ms pulse duration, with 30 ms between pulses;
d) 100 ms pulse duration, with 900 ms between pulses;
e) 100 ms pulse duration, with 500 ms between pulses;
f) 100 ms pulse duration, with 300 ms between pulses; and
g) 200 ms pulse duration, with 800 ms between pulses.

Cycles a) and d) correspond to a duty cycle of 10%; cycles b) and e) correspond to a duty cycle of 16.67%; cycles c) and f) correspond to a duty cycle of 25%; and cycle g) corresponds to a duty cycle of 20%. These duty cycles may enable the radiating tip portion to be maintained at an acceptable temperature during treatment of target tissue, whilst enabling the target tissue to be effectively treated.

In some embodiments, a length of the radiating tip portion may be equal to or greater than 140 mm. Coaxial cables which are typically used in electrosurgical instruments (e.g. the Sucoform 86 coaxial cable) often have a heavily tinned outer jacket to enable longitudinal actuation of the cable. However, this may result in the coaxial cable being relatively stiff, such that it may require a large force to bend the coaxial cable. This may cause a large amount of friction when the device is moved through a bend, e.g. in an instrument channel of a surgical scoping device. This may impede accurate control of a position of the radiating tip portion. The inventors have realised that having a long radiating tip portion may facilitate bending of the instrument near its distal end, as the radiating tip portion may have a greater flexibility compared to the coaxial cable. By making the radiating tip portion 140 mm or longer, it may be possible to avoid having to move the coaxial cable through a bent distal portion of the surgical scoping device. This may, for example, facilitate deploying the radiating tip portion where a distal portion of the surgical scoping device is in retroflex. This configuration may be particularly beneficial for use in the pancreas, where it may be necessary to have a distal portion of the instrument in retroflex.

In some embodiments, the proximal coaxial transmission line may comprise: an inner conductor that extends from a distal end of the flexible coaxial cable, the inner conductor being electrically connected to a centre conductor of the flexible coaxial cable; a proximal dielectric sleeve mounted around the inner conductor; and an outer conductor mounted around the proximal dielectric, wherein the distal needle tip comprises a distal dielectric sleeve mounted around the inner conductor, and wherein a distal portion of the outer conductor overlays a proximal portion of the distal dielectric sleeve. The distal dielectric sleeve may be secured by crimping or the like.

The outer conductor may be a conductive tube, e.g. formed from nitinol, a material that exhibits longitudinal rigidity sufficient to transmit a force capable of penetrating target tissue. Preferably the conductive tube also exhibits lateral flex suitable to enable the instrument to travel through the instrument channel of a surgical scoping device. Advantageously, nitinol may provide sufficient longitudinal rigidity for piercing the duodenum wall, to enable treatment of tissue in the pancreas, whilst still providing a high degree of lateral flexibility. The distal needle tip may be substantially rigid, to facilitate insertion into biological tissue.

The inner conductor may be formed from a material with high conductivity, e.g. silver. The inner conductor may have a diameter that is less than the diameter of the centre conductor of the flexible coaxial cable. This may facilitate bending of the radiating tip portion. For example, the diameter of the inner conductor may be 0.25 mm. A preferred diameter may take into account that a dominant parameter that determines loss (and heating) along the radiating tip portion is the conductor loss, which is a function of the diameter of the inner conductor. Other relevant parameters are the dielectric constants of the distal and proximal dielectric sleeves, and the diameter and material used for the outer conductor. The dimensions of the components of the proximal coaxial transmission line may be chosen to provide it with an impedance that is identical or close to the impedance of the flexible coaxial cable (e.g. around 50Ω).

The radiating tip portion may be secured to the flexible coaxial cable by a collar mounted over a junction therebetween. The collar may be electrically conductive, e.g. formed from brass. It may electrically connect the outer conductor with an outer conductor of the flexible coaxial cable.

A distal end of the distal dielectric sleeve may be sharpened, e.g. may taper to a point. Alternatively, a separate pointed tip element may be mounted at a distal end of the distal dielectric sleeve. This may facilitate insertion of the instrument into target tissue, e.g. through the duodenal or gastric wall into the pancreas.

The distal dielectric sleeve may be made from a different material to the proximal dielectric sleeve. The proximal dielectric sleeve may be made from the same material as a dielectric material of the flexible coaxial cable, e.g. PTFE or the like. In contrast, the distal dielectric sleeve may be made from any of ceramic, polyether ether ketone (PEEK), glass-filled PEEK. These materials may exhibit desirable rigidity and are capable of being sharpened. It also allows for controlling (e.g. reducing or optimising) the physical length of the radiating tip portion whilst maintaining its electric length. Thus, the distal dielectric sleeve may have a higher rigidity than the proximal dielectric sleeve. The higher rigidity of the distal dielectric sleeve may facilitate insertion of the radiating tip portion into target tissue, whilst the greater flexibility of the proximal dielectric sleeve may facilitate maneuvering of the radiating tip portion, e.g. around bends.

In some embodiments, a proximal end of the distal dielectric sleeve may include a protrusion disposed around the inner conductor, and the protrusion may be received in a complementarily shaped cavity at a distal end of the proximal dielectric sleeve. Such a configuration may improve a mechanical connection between the proximal and distal dielectric sleeves. Moreover, the protrusion may serve to increase a breakdown voltage of the radiating tip portion at a junction between the proximal dielectric sleeve and the distal dielectric sleeve, which may improve an electrical safety of the radiating tip portion.

The distal needle tip may be configured to operate as a half wavelength transformer to deliver the microwave energy from the distal needle tip. An advantage of configuring the distal needle tip as a half wavelength transformer may be to minimise reflections at the interface between components, e.g. between the coaxial cable and proximal coaxial transmission line, and between the proximal coaxial transmission line and the distal needle tip. A reflection coefficient at the latter interface is typically larger due to a larger variation in impedance. The half wavelength configuration may minimise these reflections so that the dominant reflection coefficient becomes that of the interface between the proximal coaxial transmission line and the tissue. The impedance of the proximal coaxial transmission line may be selected to be identical or close to the expected tissue impedance to provides a good match at the frequency of the microwave energy.

In some embodiments, the electrosurgical system may further include a surgical scoping device having a flexible insertion cord for insertion into a patient's body, the flexible insertion cord having an instrument channel running along its length, and wherein the electrosurgical instrument is dimensioned to be received within the instrument channel.

The electrosurgical system discussed herein may also be suitable for treating tissue in treatment sites that are awkward to reach, e.g. the pancreas or lungs, due to the small-diameter radiating tip portion.

The term "surgical scoping device" may be used herein to mean any surgical device provided with an insertion cord that is a rigid or flexible (e.g. steerable) conduit that is introduced into a patient's body during an invasive procedure. The insertion cord may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less. In embodiments of the invention, the surgical scoping device may be an ultrasound-enabled endoscope. For example, the surgical scoping device may be an ultrasound-enabled bronchoscope, where the insertion cord is adapted for insertion through a patient's airway into the bronchial tree. The bronchoscope may comprise one or more ultrasound transducers at a distal end of the insertion cord. The ultrasound transducers may be operable to assist insertion and position of the electrosurgical instrument. In particular, they may be arranged to generate ultrasound images of the radiating tip as it extends from the distal end of the instrument channel (and beyond the catheter) to penetrate tissue on its way to the treatment site.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate instrument. In use, the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Preferred spot frequencies for microwave EM energy include: 915 MHz, 2.45 GHz, 3.3 GHz, 5.8 GHz, 10 GHz, 14.5 GHz and 24 GHz. 5.8 GHz may be preferred. The device may deliver energy at more than one of these microwave frequencies.

The term "radiofrequency" or "RF" may be used to indicate a frequency between 300 kHz and 400 MHz. The term "low frequency" or "LF" may mean a frequency in the range 30 kHz to 300 kHz.

BRIEF DESCRIPTION OF THE DRAWINGS

Embodiments of the invention are discussed below with reference to the accompanying drawings, in which:

FIG. 8b is a perspective view of a distal tip of the radiating tip portion of FIG. 8a;

FIG. 9b is a schematic cross-sectional diagram of a distal portion of the radiating tip portion of FIG. 9a;

DETAILED DESCRIPTION; FURTHER OPTIONS AND PREFERENCES

Figure 1:
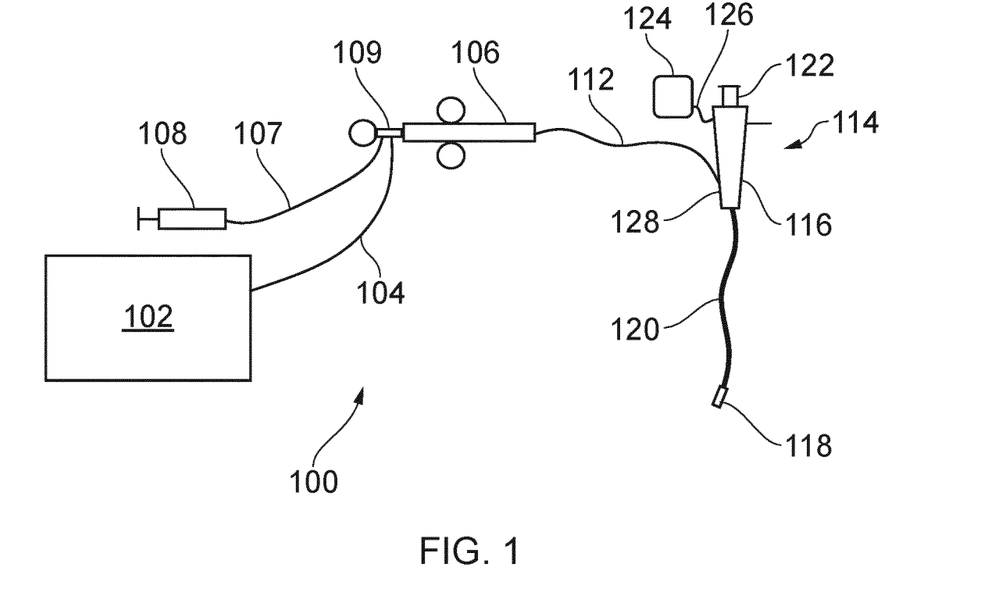
FIG. 1 is a schematic diagram of an electrosurgical system for tissue ablation that is an embodiment of the invention.

FIG. 1 is a schematic diagram of an electrosurgical system 100 that is an embodiment of the invention. The electrosurgical system 100 is capable of supplying microwave energy to a distal end of an invasive electrosurgical instrument to perform tissue ablation. The electrosurgical system is also capable of supplying a fluid, e.g. a liquid medicament or a cooling fluid, to a distal end of the invasive electrosurgical instrument. The system 100 comprises an electrosurgical generator 102 for controllably supplying microwave energy. The electrosurgical generator is configured to supply pulsed microwave energy, as discussed in more detail below. A suitable generator for this purpose is described in WO 2012/076844, which is incorporated herein by reference. The electrosurgical generator 102 may be arranged to monitor reflected signals received back from the instrument in order to determine an appropriate power level for delivery. For example, the generator 102 may be arranged to calculate an impedance seen at the distal end of the instrument in order to determine an optimal delivery power level.

The electrosurgical system 100 further includes an interface joint 106 that is connected to the electrosurgical generator 102 via an interface cable 104. The interface joint 106 is also connected via a fluid flow line 107 to a fluid delivery device 108, such as a syringe. In some examples, the system may be arranged, additionally or alternatively, to aspirate fluid from a treatment site. In this scenario, the fluid flow line 107 may convey fluid away from the interface joint 106 to a suitable collector (not shown). The aspiration mechanism may be connected at a proximal end of the fluid flow line 107.

The interface joint 106 may house an instrument control mechanism for controlling a position of the electrosurgical instrument. The control mechanism may be used to control a longitudinal position of the electrosurgical instrument, and/or bending of a distal end of the electrosurgical instrument. The Control mechanism is operable by sliding a trigger, to control a longitudinal (back and forth) movement of one or more control wires or push rods (not shown). If there is a plurality of control wires, there may be multiple sliding triggers on the interface joint to provide full control. A function of the interface joint 106 is to combine the inputs from the generator 102, fluid delivery device 108 and instrument control mechanism into a single flexible shaft (or electrosurgical instrument) 112, which extends from the distal end of the interface joint 106.

The electrosurgical system further includes a surgical scoping device 114, which in embodiment of the present invention may comprise an endoscopic ultrasound device. The flexible shaft 112 is insertable through an entire length of an instrument (working) channel of the surgical scoping device 114.

The surgical scoping device 114 comprises a body 116 having a number of input ports and an output port from which an instrument cord 120 extends. The instrument cord 120, which is illustrated in more detail in FIG. 2, comprises an outer jacket which surrounds a plurality of lumens. The plurality of lumens convey various things from the body 116 to a distal end of the instrument cord 120. One of the plurality of lumens is the instrument channel discussed above. Other lumens may include a channel for conveying optical radiation, e.g. to provide illumination at the distal end or to gather images from the distal end. The body 116 may include an eye piece 122 for viewing the distal end.

An endoscopic ultrasound device typically provides an ultrasound transducer on a distal tip of the instrument cord, beyond an exit aperture of the instrument channel. Signals from the ultrasound transducer may be conveyed by a suitable cable 126 back along the instrument cord to a processor 124, which can generate images in a known manner. The instrument channel may be shaped within the instrument cord to direct an instrument exiting the instrument channel through the field of view of the ultrasound system, to provide information about the location of the instrument at the target site.

The flexible shaft 112 has a distal assembly 118 (not drawn to scale in FIG. 1) that is shaped to pass through the instrument channel of the surgical scoping device 114 and protrude (e.g. inside the patient) at the distal end of the instrument cord.

The structure of the distal assembly 118 discussed below may be particularly designed for use with an endoscopic ultrasound (EUS) device. The maximum outer diameter of the distal assembly 118 is equal to or less than 1.0 mm, e.g. less than 0.95 mm or 0.90 mm. The length of the flexible shaft can be equal to or greater than 1.2 m.

The body 116 includes an input port 128 for connecting to the flexible shaft 112. As explained below, a proximal portion of the flexible shaft may comprise a conventional coaxial cable capable of conveying the pulsed microwave energy from the electrosurgical generator 102 to the distal assembly 118. Example coaxial cables that are physically capable of fitting down the instrument channel of an EUS device are available with the following outer diameters: 1.19 mm (0.047"), 1.35 mm (0.053"), 1.40 mm (0.055"), 1.60 mm (0.063"), 1.78 mm (0.070"). Custom-sized coaxial cables (i.e. made to order) may also be used.

In order to control a position of a distal end of the instrument cord 120, the body 116 may further include a control actuator that is mechanically coupled to the distal end of the instrument cord 120 by one or more control wires (not shown), which extend through the instrument cord 120. The control wires may travel within the instrument channel or within their own dedicated channels. The control actuator may be a lever or rotatable knob, or any other known catheter manipulation device. The manipulation of the instrument cord 120 may be software-assisted, e.g. using a virtual three-dimensional map assembled from computer tomography (CT) images.

The invention may be particularly suited for treatment of the pancreas. In order to reach a target site in the pancreas, the instrument cord 120 may need to be guided through the mouth, stomach and duodenum. The electrosurgical instrument is arranged to access the pancreas by passing through the wall of the duodenum. The invention may also be particularly suited to treatment of tissue in the liver.

Figure 2:
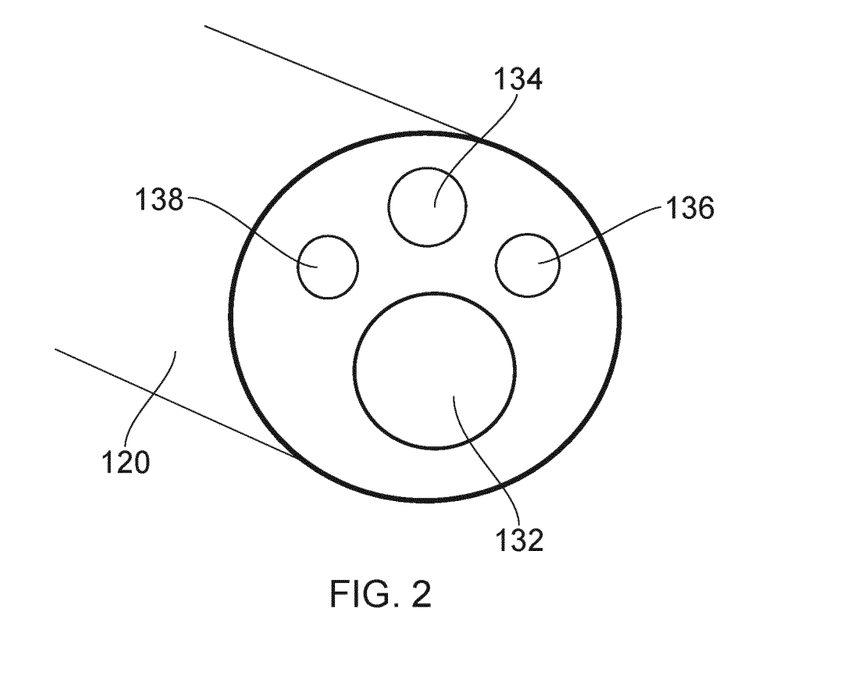
FIG. 2 is a schematic sectional view through an instrument cord of an endoscope that can be used with the present invention.

FIG. 2 is a view down the axis of the instrument cord 120. In this embodiment there are four lumens within the instrument cord 120. The largest lumen is the instrument channel 132 in which the flexible shaft 112 is received. The other lumens comprise an ultrasound signal channel 134, an illumination channel 136, and a camera channel 138 but the invention is not limited to this configuration. For example, there may be other lumens, e.g. for control wires or fluid delivery or suction.

Figure 3:
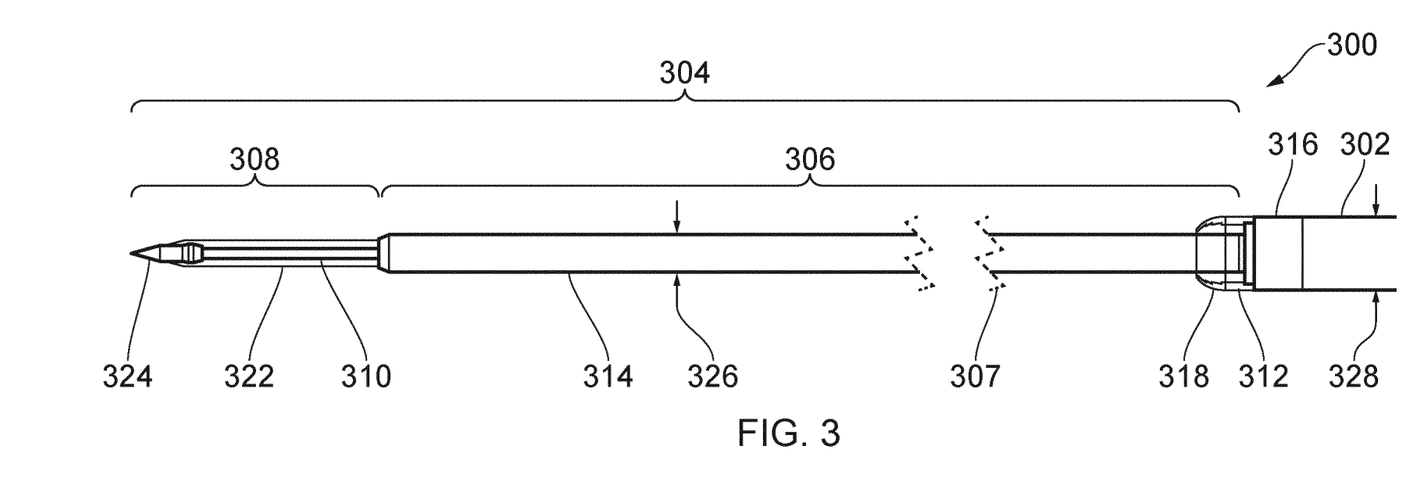
FIG. 3 is a schematic side view of an electrosurgical instrument that may be used in an electrosurgical system of the invention.
Figure 4:
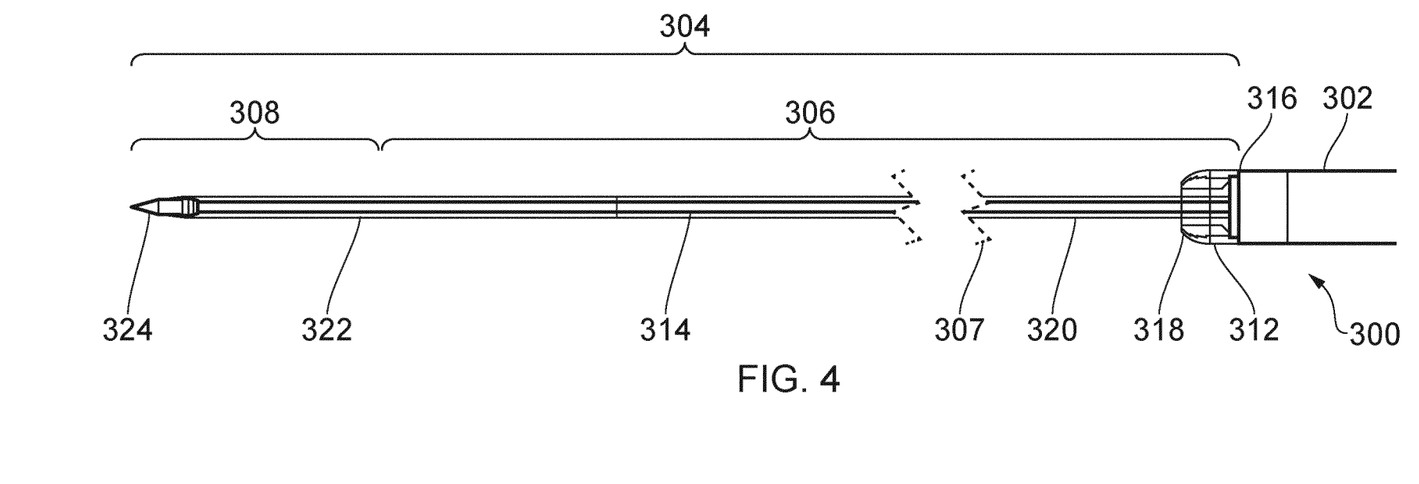
FIG. 4 is a cross-sectional diagram of the electrosurgical instrument of FIG. 3, where an outer conductor has been omitted for illustration purposes.

We will now describe an electrosurgical instrument 300 that may be part of an electrosurgical system of the invention, with reference to FIGS. 3 and 4. FIGS. 3 and 4 show side views of a distal portion of the electrosurgical instrument 300, which may correspond to the distal assembly 118 referred to above. The electrosurgical instrument 300 includes a flexible coaxial cable 302, and a radiating tip portion 304 which is connected at a distal end of the coaxial cable 302. The coaxial cable 302 may be a conventional flexible 50Ω coaxial cable suitable for conveying microwave energy. The coaxial cable includes a centre conductor and an outer conductor that are separated by a dielectric material. The coaxial cable 302 is connectable at a proximal end to a generator, e.g. to generator 102, to receive the microwave energy.

The radiating tip portion 304 includes a proximal coaxial transmission line 306 and a distal needle tip 308 formed at a distal end of the proximal coaxial transmission line 306. The proximal coaxial transmission line 306 is electrically connected to the distal end of the coaxial cable 302 to receive the electromagnetic energy from the coaxial cable 302 and convey it to the distal needle tip 308. The distal needle tip 308 is configured to deliver the received electromagnetic energy into target biological tissue. In the present example, the distal needle tip 308 is configured as a half wavelength transformer to deliver microwave energy into target biological tissue, to ablate the target tissue. In other words, an electrical length of the distal needle tip 308 corresponds to a half wavelength of the microwave energy (e.g. at 5.8 GHz). When microwave energy is delivered to the distal needle tip 308 it may radiate the microwave energy along its length into surrounding biological tissue.

An inner conductor 310 of the proximal coaxial transmission line 306 is electrically connected to the centre conductor of the coaxial cable 302. The radiating tip portion 304 is secured to the coaxial cable 302 via a collar 312 mounted over a junction between the coaxial cable 302 and the radiating tip portion 304. The collar 312 is made of a conductive material (e.g. brass), and electrically connects the outer conductor of the coaxial cable 302 to an outer conductor 314 of the proximal coaxial transmission line 306. The outer conductor 314 is formed of a tube of nitinol, which is flexible and provides a sufficient longitudinal rigidity to pierce tissue (e.g. the duodenum wall). For illustration purposes, the outer conductor 314 is omitted from FIG. 4 to reveal an inner structure of the radiating tip portion 304. Also for illustration purposes, a length of the proximal coaxial transmission line 306 has been omitted in FIGS. 3 and 4, as indicated by broken lines 307.

The proximal coaxial transmission line 306 includes a proximal dielectric sleeve 320 which is disposed around the inner conductor 310 and which spaces the inner conductor 310 from the outer conductor 314. The outer conductor 314 is formed on an outer surface of the proximal dielectric sleeve 320. A distal dielectric sleeve 322 is disposed around a distal portion of the inner conductor 310 to form the distal needle tip 308. The distal needle tip 308 further includes a pointed tip 324 at its distal end, to facilitate insertion of the radiating tip portion into target tissue. The distal dielectric sleeve 322 may be made of a different dielectric material compared to the proximal dielectric sleeve 504. In one example, the proximal dielectric sleeve 504 may be made of PTFE (e.g. it may be a PTFE tube) and the distal dielectric sleeve may be made of PEEK. Specific examples of materials that may be used in the radiating tip portion 304 are discussed below in relation to FIGS. 7-11.

A distal portion of the outer conductor 314 overlays a proximal portion of the distal dielectric sleeve 322. In this manner, a distal portion of the proximal coaxial transmission line 306 includes the proximal portion of the distal dielectric sleeve 322. The materials of the proximal and distal dielectric sleeves and the length of the overlap between the outer conductor 314 and the distal dielectric sleeve 322 may be selected in order to adjust an electrical length of the radiating tip portion 308 and impedance matching with target tissue.

The collar 312 includes a substantially cylindrical body 316 which is mounted on the distal end of the coaxial cable 302 and which is electrically connected to the outer conductor of the coaxial cable 302. The collar 312 further includes a distal portion 318 which extends from the body 316 of the collar 312 to a proximal end of the outer conductor 314 of the proximal coaxial transmission line 306. The distal portion 318 of the collar 312 includes a distal surface which is rounded. This may reduce friction between the electrosurgical instrument 300 and an instrument channel of a surgical scoping device when the electrosurgical instrument 300 is moved along the channel, by avoiding sharp edges at the interface between the coaxial cable 302 and the radiating tip portion 304. This may also facilitate moving the electrosurgical instrument along the channel when the channel is in retroflex.

A maximum outer diameter of the radiating tip portion 304 is indicated in FIG. 3 by arrows 326. In the present example, the maximum outer diameter of the radiating tip portion 304 corresponds to an outer diameter of the outer conductor 314, as this is the component of the radiating tip portion 304 having the largest outer diameter. The maximum outer diameter of the radiating tip portion 304 is 1.0 mm or less. For example, it may be 1.0 mm, 0.95 mm or 0.90 mm. This may ensure that a size of an insertion hole produced by the radiating tip portion 304 when it is inserted into target tissue is small, which may minimise bleeding. This may make the electrosurgical instrument 300 particularly suited to use in highly vascularised regions of the body, e.g. in the liver, where excessive bleeding may be an issue.

An outer diameter of the coaxial cable 302 is indicated by arrows 328 in FIG. 3. The outer diameter of the coaxial cable 302 is larger than the maximum outer diameter of the radiating tip portion 304. For example, the outer diameter of the coaxial cable 302 may be between 1.19 mm and 2.0 mm, or it may be greater than 2.0 mm. By providing the radiating tip portion 304 with a smaller maximum outer diameter than the coaxial cable, it is possible to increase the flexibility of the radiating tip portion 304 relative to the coaxial cable 302. This may facilitate maneuvering the radiating tip portion 304 to a particular treatment location. At the same time, by providing the coaxial cable 302 with a larger diameter, transmission losses (e.g. due to heating) in the coaxial cable 302 may be reduced, as transmission losses are generally related to the diameter of the coaxial cable 302. This may enable microwave energy to be conveyed more efficiently along the coaxial cable 302 to the radiating tip portion 304.

In some embodiments, the electrosurgical instrument 300 may be housed in a catheter (not shown). The electrosurgical instrument 300 may be movable relative to the catheter, so that the radiating tip portion 304 can be retracted inside the catheter when not in use. This may serve to protect the radiating tip portion, and prevent it from catching on the instrument cord when it is inserted into the instrument cord of a surgical scoping device.

The radiating tip portion 304 may have a length equal to or greater than 30 mm, e.g. 40 mm. In this manner, the radiating tip portion 304 may be long enough for the distal needle tip 308 to reach a treatment site, without having to insert a portion of the coaxial cable 302 into tissue. In some cases the radiating tip portion 304 may have a length of 140 mm or greater. The inventors have found that this may facilitate inserting the electrosurgical instrument 300 into an instrument cord where a distal portion of the instrument cord is in retroflex, as it may avoid having to push the more rigid coaxial cable 302 through the distal portion of the instrument cord.

Figure 5:
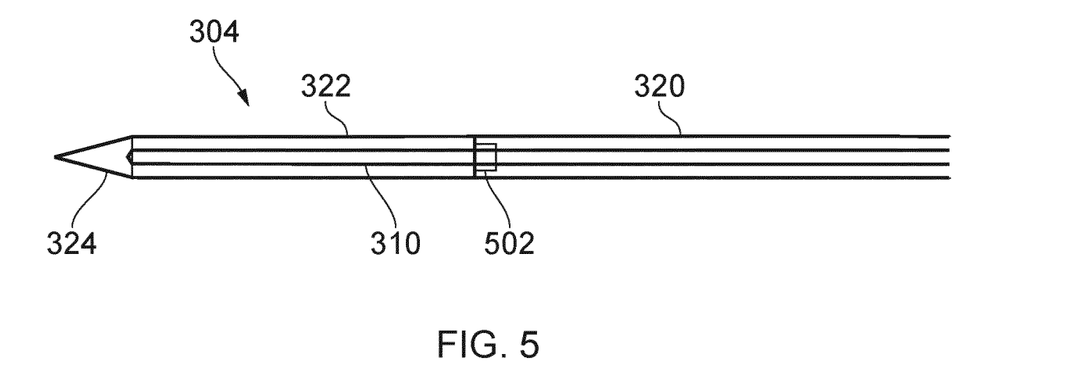
FIG. 5 is a cross-sectional diagram of a distal section of the electrosurgical instrument of FIG. 3.

FIG. 5 illustrates an interface between the proximal dielectric sleeve 320 and the distal dielectric sleeve 322 in more detail. FIG. 5 shows a cross-sectional view of a distal section of the radiating tip portion 304. For illustration purposes, the outer conductor 314 is omitted from FIG. 5. A proximal end of the distal dielectric sleeve 322 includes a protrusion 502 which extends from the proximal end of the distal dielectric sleeve 322. The protrusion 502 has a generally cylindrical shape, with an outer diameter smaller than that of the distal dielectric sleeve 322, and is disposed around the inner conductor 310. The proximal dielectric sleeve 320 includes a cavity having a shape complementary to that of the protrusion 502, in which the protrusion 502 is received. Thus, the proximal dielectric sleeve 320 steps around the protrusion 502. As the protrusion 502 of the distal dielectric sleeve 322 is received in the proximal dielectric sleeve 320, this serves to provide a strong mechanical connection between the distal and proximal dielectric sleeves. Additionally, the protrusion 502 may serve to increase a breakdown voltage of the radiating tip portion 304 at the interface between the distal dielectric sleeve 322 and the proximal dielectric sleeve 320. This may improve an electrical safety of the radiating tip portion 304.

As the radiating tip portion 304 of electrosurgical instrument has a small diameter (i.e. 1.0 mm or less), it may heat up rapidly when microwave energy is delivered to it. This may result in inefficient delivery of microwave energy to the distal needle tip. Heating of the radiating tip portion 304 may also cause damage to healthy surrounding tissue. The inventors have overcome this drawback by configuring the electrosurgical generator (e.g. electrosurgical generator 102) of the electrosurgical system of the invention to deliver the microwave energy in pulses. The inventors have found that pulsed delivery of microwave energy may avoid or reduce heating effects in the radiating tip portion, so that the radiating tip portion may be maintained at an acceptable temperature during a surgical procedure.

In order to avoid heating of the radiating tip portion during application of microwave energy, a pulse duration of the microwave pulses may be set to be greater than a thermal response time of the radiating tip portion. In this manner, the radiating tip portion may not have time to react thermally to the pulsed microwave energy on the timescale of the microwave pulses. The thermal response time of the radiating tip portion may be measured experimentally, by determining an amount of time taken for a temperature of the radiating tip portion to increase by a given amount (e.g. 5° C.) when microwave energy at a given power level (e.g. a power level to be used during an electrosurgical procedure) is delivered to the radiating tip portion. The pulse duration may then be set accordingly, to ensure that the temperature of the radiating tip portion remains at an acceptable temperature over the course of an electrosurgical procedure.

The inventors have found that configuring the electrosurgical generator to deliver pulsed microwave energy with a duty cycle of 25% or less may avoid or reduce heating effects in the radiating tip portion so that it may be maintained at an acceptable temperature during use. The electrosurgical generator may be configured to deliver microwave energy according to one of the following example cycles:
 a) 10 ms pulse duration, with 90 ms between pulses;
 b) 10 ms pulse duration, with 50 ms between pulses;
 c) 10 ms pulse duration, with 30 ms between pulses;
 d) 100 ms pulse duration, with 900 ms between pulses;
 e) 100 ms pulse duration, with 500 ms between pulses;
 f) 100 ms pulse duration, with 300 ms between pulses; and
 g) 200 ms pulse duration, with 800 ms between pulses.
Cycles a) and d) correspond to a duty cycle of 10%; cycles b) and e) correspond to a duty cycle of 16.67%; cycles c) and f) correspond to a duty cycle of 25%; and cycle g) corresponds to a duty cycle of 20%.

Figure 6:
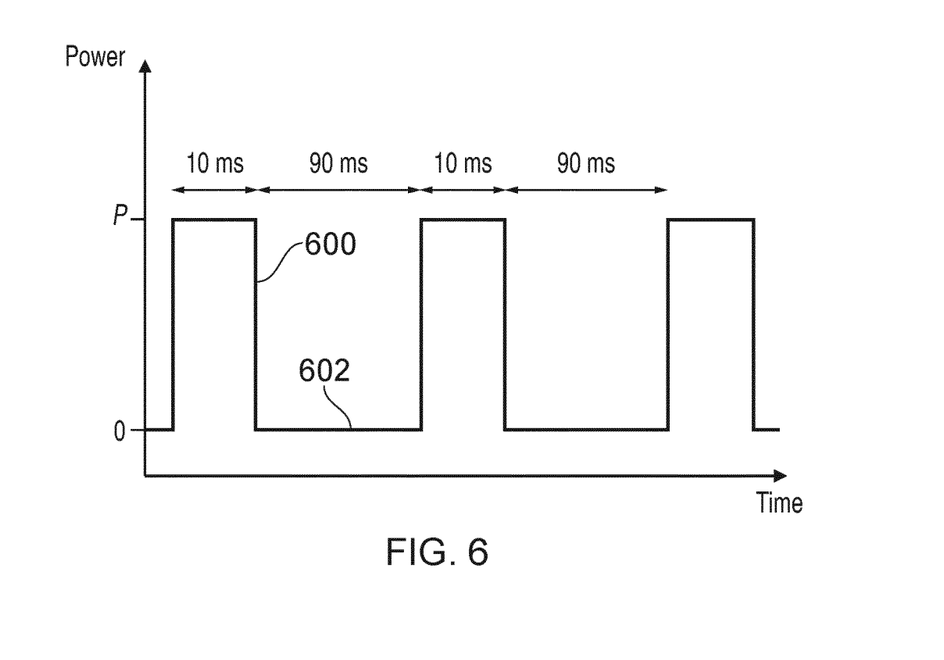
FIG. 6 is a graph showing power delivery profile of pulsed microwave energy supplied by an electrosurgical generator that is part of an electrosurgical system of the invention.

FIG. 6 illustrates a power delivery profile according to cycle a) given above. The power delivery profile of FIG. 6 shows power of microwave energy supplied by the electrosurgical generator against time. The power delivery profile includes a series of microwave pulses 600, each having a duration of 10 ms. The microwave pulses 600 are separated by intervals 602, each having a duration of 90 ms. The microwave pulses 600 each have a power P, as indicated in FIG. 6. During the intervals 602, no microwave energy is supplied by the electrosurgical generator (i.e. the supplied power is 0 W). Each of the pulses 600 is identical, and includes a constant power level. Note that the power delivery profile of FIG. 6 is not drawn to scale. In other examples, the power level of a microwave pulse may vary over the course of the pulse, depending on a desired energy delivery profile. In some cases, a microwave pulse cycle may include pulses having different durations and/or power levels.

We will now describe specific examples of radiating tip portions of electrosurgical instruments that may be used in an electrosurgical system of the invention, with reference to FIGS. 7-11. The radiating tip portions described below may, for example, be used instead of the radiating tip portion 304 of electrosurgical instrument 300 discussed above. Radiating tip portions 700, 800, 900, 1000 and 1100 discussed below each have a similar overall configuration. Similarly to radiating tip portion 304, each of radiating tip portions 700, 800, 900, 1000 and 1100 has an inner conductor electrically connected to a centre conductor of a coaxial cable (not shown), and an outer conductor electrically connected to an outer conductor of the coaxial cable. The radiating tip portions 700, 800, 900, 1000 and 1100 each further include a proximal dielectric sleeve and a distal dielectric sleeve disposed around the inner conductor, in order to form a proximal transmission line and a distal needed tip as discussed above in relation to radiating tip portion 304.

Figure 7:
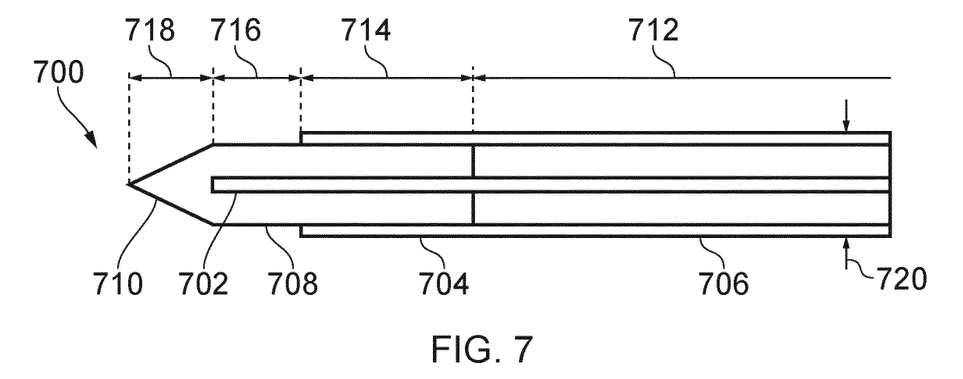
FIG. 7 is a schematic cross-sectional diagram of a radiating tip portion that may be used in an electrosurgical system of the invention.

FIG. 7 shows a cross-sectional view of a distal section of a radiating tip portion 700. A proximal dielectric sleeve 706 of radiating tip portion 700 may be made of a flexible insulating material, e.g. PTFE. A distal dielectric sleeve 708 of radiating tip portion 700 is made of a cylindrical piece of Zirconia. A distal tip 710 of the distal dielectric sleeve 708 is sharpened, to facilitate insertion of the radiating tip portion 700 into tissue. Making the distal dielectric sleeve 708 of Zirconia may provide a rigid distal needle tip to the radiating tip portion 700, which may facilitate piercing of tissue. Use of Zirconia may also enable a physical length of the radiating tip portion to be shortened, whilst maintaining a desired electrical length.

Example dimensions of the radiating tip portion 700 are shown in FIG. 7. The dimension indicated by reference numeral 712, which corresponds to a length of the proximal dielectric sleeve 706, may be 37 mm. Note the total length of the proximal dielectric sleeve 706 is not shown in FIG. 7. The dimension indicated by reference numeral 714, which corresponds to an overlap between an outer conductor 704 of the radiating tip portion 700 and the distal dielectric sleeve 708, may be 3.6 mm. The dimension indicated by reference numeral 716, which corresponds to a length of an inner conductor 702 of the radiating tip portion 700 that protrudes beyond a distal end of the outer conductor 704, may be 1.5 mm. The dimension indicated by reference numeral 718, which corresponds to a length of the distal tip 710, may be 1.5 mm. A maximum outer diameter of the radiating tip portion 700, indicated by reference numeral 720, is 1.0 mm or less. The junction between the distal dielectric sleeve 708 and the proximal dielectric sleeve may be crimped, e.g. around the outer surface of the outer conductor 704, 706, in order to strengthen the connection between the distal dielectric sleeve 708 and the remainder of the instrument.

Figure 8A:
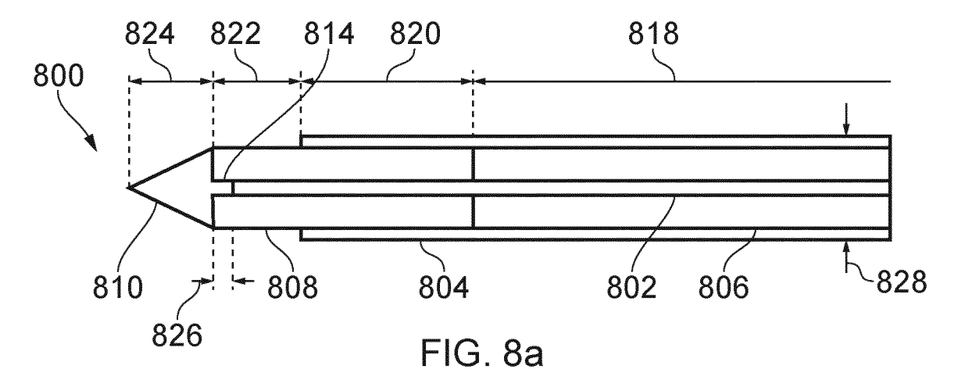
FIG. 8a is a schematic cross-sectional diagram of a radiating tip portion that may be used in an electrosurgical system of the invention.
Figure 8B:
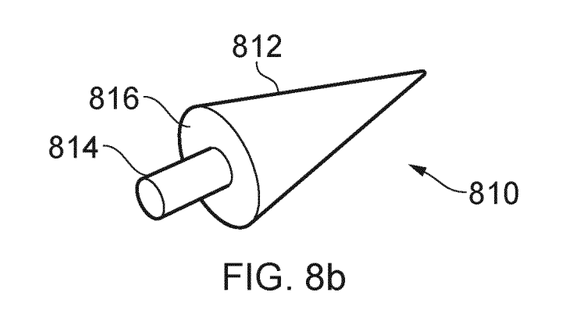

FIG. 8a shows a cross-sectional view of a distal section of a radiating tip portion 800. A proximal dielectric sleeve 806 of radiating tip portion 800 may be made of a flexible tube of insulating material, e.g. PTFE. A distal dielectric sleeve 808 of radiating tip portion 800 is made of a cylindrical piece of Zirconia. The distal dielectric sleeve 808 includes a bore in which the inner conductor is received. A distal tip 810 made of Zirconia is mounted at a distal end of the distal dielectric sleeve 808. A perspective view of the distal tip 810 is shown in FIG. 8b. The distal tip 810 has a conical body 812 forming a pointed tip, to facilitate insertion of the radiating tip portion 800 into tissue. The distal tip 810 includes a protrusion 814 extending from a proximal face 816 of the conical body 812. The protrusion of the distal tip 810 is received in the bore in the distal dielectric sleeve 808, where it is secured in placed. The tip may be secured using an adhesive. Additionally or alternatively, the tip may be secured by crimping the distal end.

Example dimensions of the radiating tip portion 800 are shown in FIG. 8a. The dimension indicated by reference numeral 818, which corresponds to a length of the proximal dielectric sleeve 806, may be 37 mm. Note the total length of the proximal dielectric sleeve 806 is not shown in FIG. 8a. The dimension indicated by reference numeral 820, which corresponds to an overlap between an outer conductor 804 of the radiating tip portion 800 and the distal dielectric sleeve 808, may be 3.6 mm. The dimension indicated by reference numeral 822, which corresponds to a length of the distal dielectric sleeve 808 that protrudes beyond a distal end of the outer conductor 804, may be 2.0 mm. The dimension indicated by reference numeral 824, which corresponds to a length of the conical body 812 of the distal tip 810, may be 1.5 mm. The dimension indicated by reference numeral 826, which corresponds to a length of the protrusion 814, may be 0.5 mm. A maximum outer diameter of the radiating tip portion 800, indicated by reference numeral 828, is 1.0 mm or less.

Figure 9A:
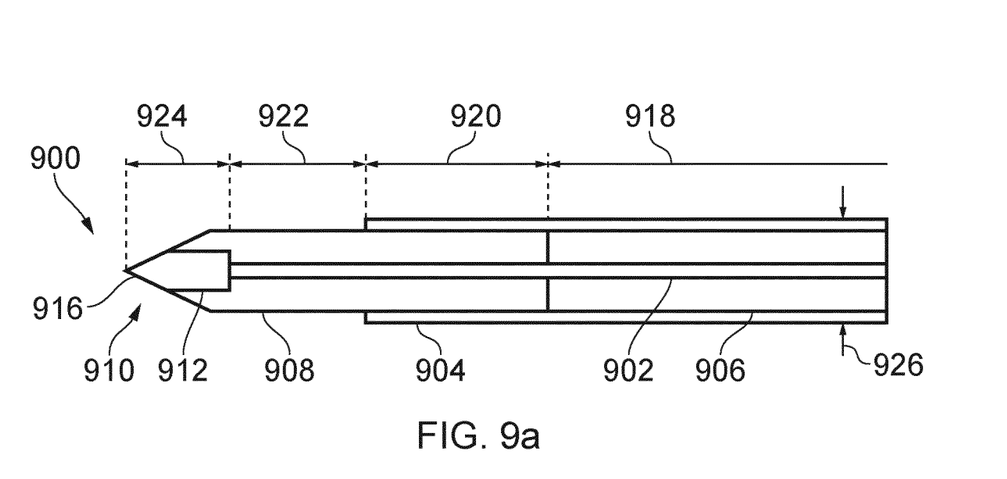
FIG. 9a is a schematic cross-sectional diagram of a radiating tip portion that may be used in an electrosurgical system of the invention.

FIG. 9a shows a cross-sectional view of a distal section of a radiating tip portion 900. A proximal dielectric sleeve 906 of the radiating tip portion 900 may be made of a flexible tube of insulating material, e.g. PTFE. A distal dielectric sleeve 908 of the radiating tip portion 900 is made of a cylindrical piece of Polyether ether ketone (PEEK). The distal dielectric sleeve 908 includes a cavity at a distal end thereof in which a distal tip 910 made of Zirconia is received. A "push-fit" connection is formed between the distal tip 910 and the distal dielectric sleeve 908.

Figure 9B:
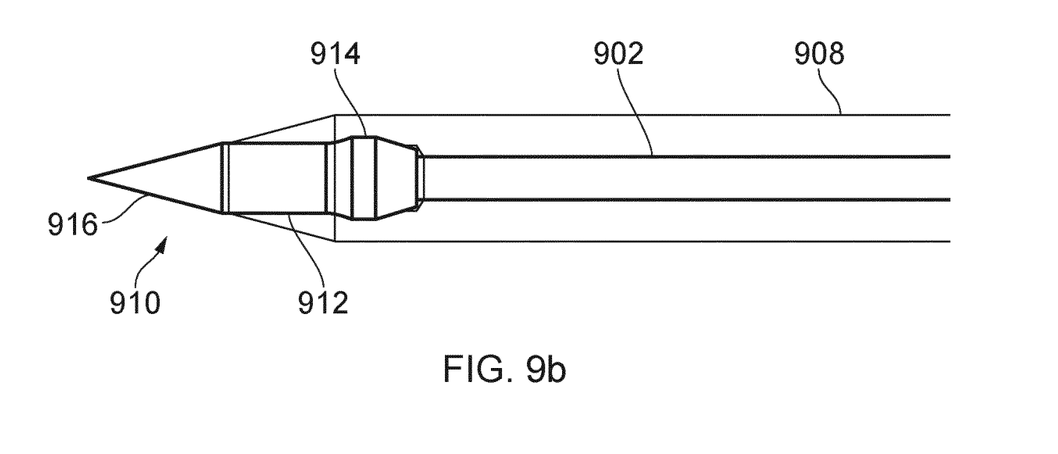

FIG. 9b shows the connection between the distal tip 910 and the distal dielectric sleeve 908 in greater detail. The distal tip includes a body 912 which is received in the cavity in the distal dielectric sleeve 908. The body 912 includes a bump 914 on its outer surface, which is arranged to press outwards against the distal dielectric sleeve 908, in order to retain the distal tip 910 in the cavity. Thus, the distal tip 910 may be automatically retained within the cavity once it has been inserted into the cavity. The distal tip 910 may further be secured in the cavity using adhesive. The distal tip 910 further includes a conical portion 916, which forms a pointed tip a distal end of the radiating tip portion 900. An outer surface of the distal dielectric sleeve 908 is tapered at an angle matching a tapering angle of the conical portion 916, so that an outer surface of the radiating tip portion 900 is smooth. Making the distal tip 910 out of Zirconia may enable a sharper distal tip to be provided, as Zirconia may have a higher rigidity than PEEK.

Example dimensions of the radiating tip portion 900 are shown in FIG. 9a. The dimension indicated by reference numeral 918, which corresponds to a length of the proximal dielectric sleeve 906, may be 37 mm. Note the total length of the proximal dielectric sleeve 906 is not shown in FIG. 9a. The dimension indicated by reference numeral 920, which corresponds to an overlap between an outer conductor 904 of the radiating tip portion 900 and the distal dielectric sleeve 908, may be 7.0 mm. The dimension indicated by reference numeral 922, which corresponds to a length of an inner conductor 902 of the radiating tip portion 900 that protrudes beyond a distal end of the outer conductor 904, may be 5.0 mm. The dimension indicated by reference numeral 924, which corresponds to a length of distal tip 910, may be 2.0 mm. A maximum outer diameter of the radiating tip portion 900, indicated by reference numeral 926, is 1.0 mm or less.

Figure 10:
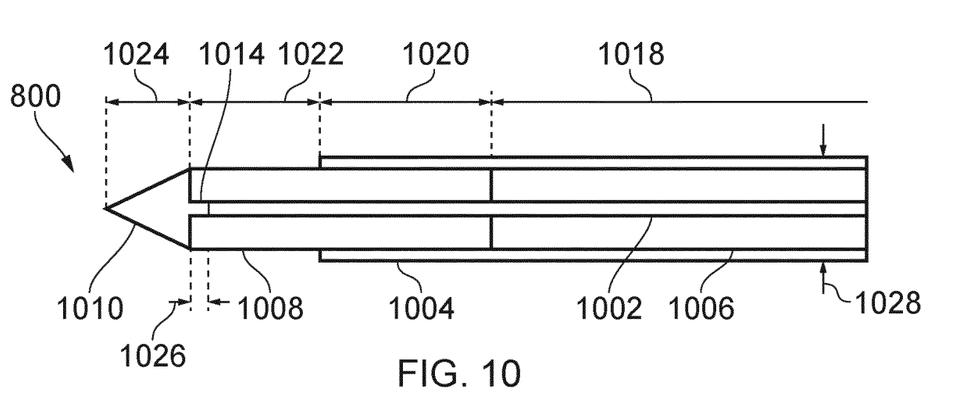
FIG. 10 is a schematic cross-sectional diagram of a radiating tip portion that may be used in an electrosurgical system of the invention.

FIG. 10 shows a cross-sectional view of a distal section of a radiating tip portion 1000. A proximal dielectric sleeve 1006 of radiating tip portion 1000 may be made of a flexible tube of insulating material, e.g. PTFE. A distal dielectric sleeve 1008 of radiating tip portion 1000 is made of a cylindrical piece of PEEK. Similarly to radiating tip portion 800, radiating tip 1000 includes a distal tip 1010 made of Zirconia mounted at a distal end of the distal dielectric sleeve 1008. The distal tip 1010 has a similar configuration to distal tip 810 shown in FIG. 8b, i.e. it includes a conical body and a protrusion 1014 that is received in a bore in the distal dielectric sleeve 1008.

Example dimensions of the radiating tip portion 1000 are shown in FIG. 10. The dimension indicated by reference numeral 1018, which corresponds to a length of the proximal dielectric sleeve 1006, may be 37 mm. Note the total length of the proximal dielectric sleeve 1006 is not shown in FIG. 10. The dimension indicated by reference numeral 1020, which corresponds to an overlap between an outer conductor 1004 of the radiating tip portion 1000 and the distal dielectric sleeve 1008, may be 6.0 mm. The dimension indicated by reference numeral 1022, which corresponds to a length of the distal dielectric sleeve 1008 that protrudes beyond a distal end of the outer conductor 1004, may be 5.5 mm. The dimension indicated by reference numeral 1024, which corresponds to a length of the conical body of the distal tip 810, may be 1.5 mm. The dimension indicated by reference numeral 1026, which corresponds to a length of the protrusion 1014, may be 0.5 mm. A maximum outer diameter of the radiating tip portion 1000, indicated by reference numeral 1028, is 1.0 mm or less.

Figure 11:
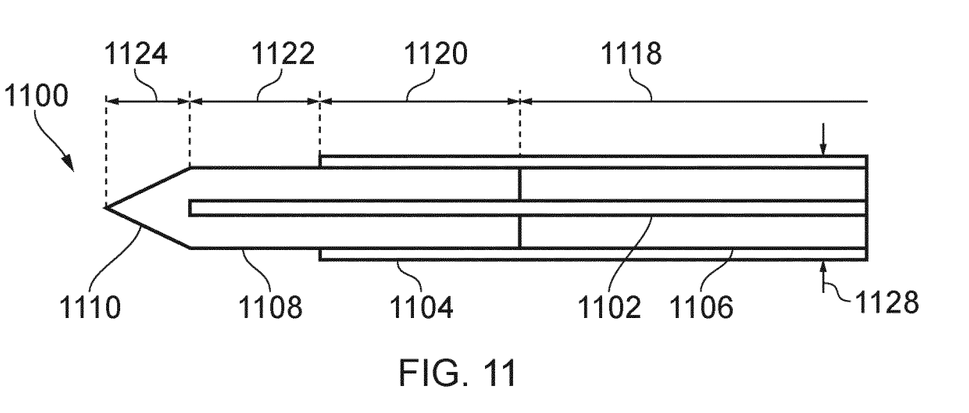
FIG. 11 is a schematic cross-sectional diagram of a radiating tip portion that may be used in an electrosurgical system of the invention.

FIG. 11 shows a cross-sectional view of a distal section of a radiating tip portion 1100. A proximal dielectric sleeve 1106 of radiating tip portion 1100 may be made of a flexible tube of insulating material, e.g. PTFE. A distal dielectric sleeve 1108 of radiating tip portion 1100 is made of a cylindrical piece of PEEK. A distal tip 1110 of the distal dielectric sleeve 1108 is sharpened, to facilitate insertion of the radiating tip portion 1100 into tissue.

Example dimensions of the radiating tip portion 1100 are shown in FIG. 11. The dimension indicated by reference numeral 1118, which corresponds to a length of the proximal dielectric sleeve 1106, may be 37 mm. Note the total length of the proximal dielectric sleeve 1106 is not shown in FIG. 11. The dimension indicated by reference numeral 1120, which corresponds to an overlap between an outer conductor 1104 of the radiating tip portion 1000 and the distal dielectric sleeve 1108, may be 6.0 mm. The dimension indicated by reference numeral 1122, which corresponds to a length of an inner conductor 1102 of the radiating tip portion 1100 that protrudes beyond a distal end of the outer conductor 1004, may be 5.5 mm. The dimension indicated by reference numeral 1024, which corresponds to a length of the distal tip 1110, may be 1.5 mm. A maximum outer diameter of the radiating tip portion 1100, indicated by reference numeral 1028, is 1.0 mm or less.

Figure 12:
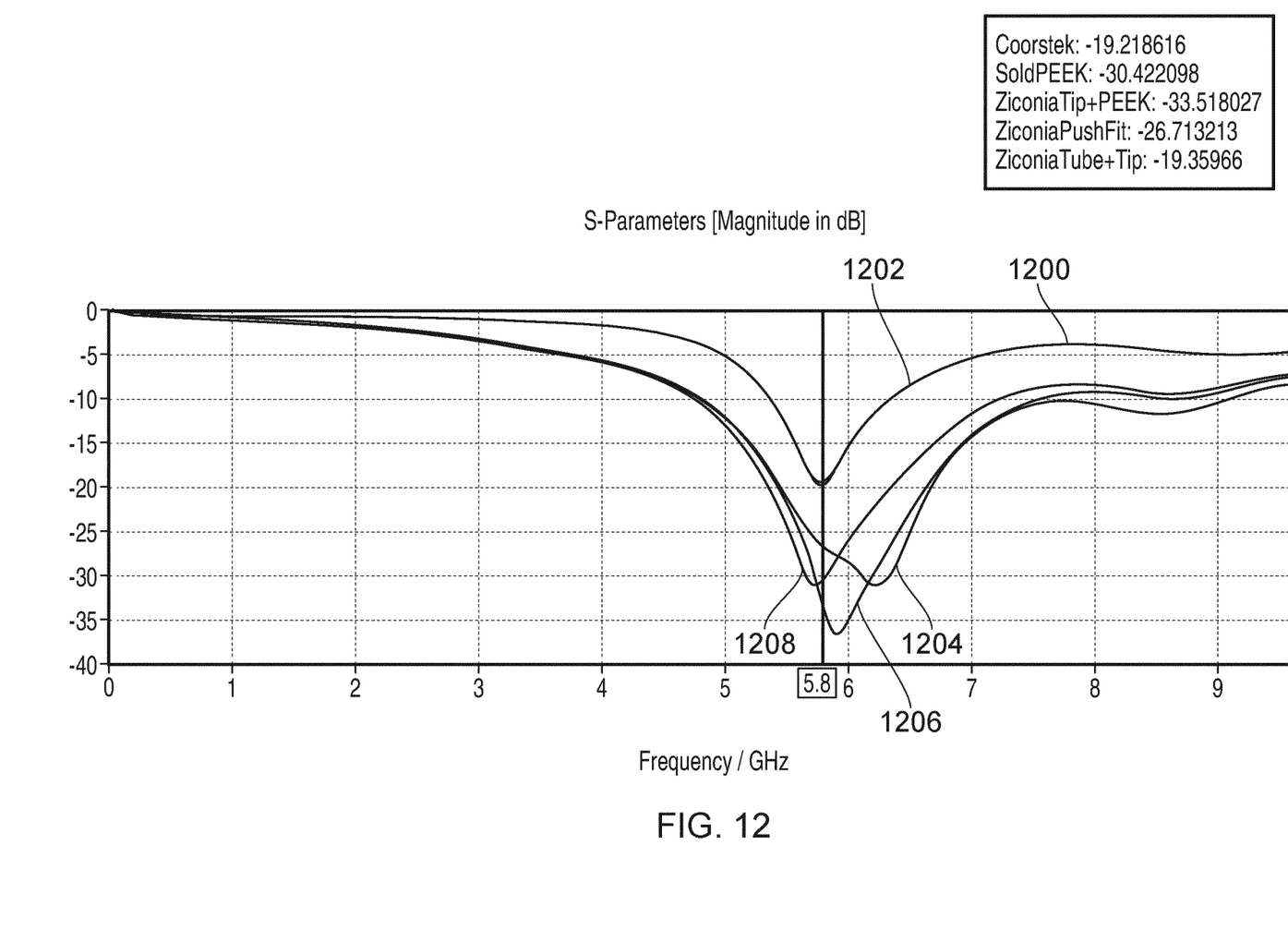
FIG. 12 shows plots of simulated return loss for electrosurgical instruments having the radiating tip portions in FIGS. 8, 8a, 9a, 10 and 11.

FIG. 12 shows simulated plots of the S-parameter (also known as the "return loss") against frequency of microwave energy for electrosurgical instruments having radiating tip portions 700, 800, 900, 1000 and 1100 described above. As is well known in the technical field, the S-parameter is a measure of the return loss of microwave energy due to impedance mismatch, and as such the S-parameter is indicative of the degree of impedance mismatch between the target tissue and the radiating tip portion. The S-parameter can be defined by the equation $P_I = SP_R$, where $P_I$ is the outgoing power in the instrument towards the tissue, $P_R$ is the power reflected back from the tissue, and S is the S-parameter. In FIG. 12, curve 1200 corresponds to a simulation for radiating tip portion 700; curve 1202 corresponds to a simulation for radiating tip portion 800; curve 1204 corresponds to a simulation for radiating tip portion 900; curve 1206 corresponds to a simulation for radiating tip portion 1000; curve 1208 corresponds to a simulation for radiating tip portion 1100. Note that curves 1200 and 1202 are very close to one another and so appear to overlap.

As shown in FIG. 12, at a microwave energy frequency of 5.8 GHz, the S-parameter is −19.2 dB for radiating tip portion 700, −19.3 dB for radiating tip portion 800, −26.7 dB for radiating tip portion 900, −33.5 dB for radiating tip portion 1000 and −30.4 dB for radiating tip portion 1100. This means that for each of these radiating tip portions, very little microwave energy is reflected back from the tissue at 5.8 GHz. This indicates a good impedance match between the radiating tip portions and biological tissue at the operating frequency of 5.8 GHz, and that microwave energy may be efficiently delivered from the radiating tip into the tissue at this frequency.

The invention claimed is:

1. An electrosurgical system for treating biological tissue, the electrosurgical system comprising:
   an electrosurgical generator configured to supply pulsed microwave energy; and
   an electrosurgical instrument comprising:
   a flexible coaxial cable arranged to convey the pulsed microwave energy; and
   a radiating tip portion connected at a distal end of the flexible coaxial cable and configured to receive the pulsed microwave energy, wherein the radiating tip portion has a maximum outer diameter that is 1.0 mm or less, and wherein the maximum outer diameter of the radiating tip portion is smaller than an outer diameter of the flexible coaxial cable, the radiating tip portion comprising:
   a proximal coaxial transmission line for conveying the pulsed microwave energy; and
   a distal needle tip mounted at a distal end of the proximal coaxial transmission line, the distal needle tip being arranged to deliver the pulsed microwave energy into biological tissue,
   wherein a pulse duration of the pulsed microwave energy is shorter than a thermal response time of the radiating tip portion.

2. The electrosurgical system according to claim 1, wherein the electrosurgical generator is configured to supply the pulsed microwave energy with a duty cycle of 25% or less.

3. The electrosurgical system according to claim 2, wherein a pulse duration of the pulsed microwave energy is between 10 ms and 200 ms.

4. The electrosurgical system according to claim 3, wherein the pulsed microwave energy is delivered according to one of the following cycles:
   a) 10 ms pulse duration, with 90 ms between pulses;
   b) 10 ms pulse duration, with 50 ms between pulses;
   c) 10 ms pulse duration, with 30 ms between pulses;
   d) 100 ms pulse duration, with 900 ms between pulses;
   e) 100 ms pulse duration, with 500 ms between pulses;
   f) 100 ms pulse duration, with 300 ms between pulses; and
   g) 200 ms pulse duration, with 800 ms between pulses.

5. The electrosurgical system according to claim 1, wherein a length of the radiating tip portion is equal to or greater than 140 mm.

6. The electrosurgical system according to claim 1, wherein the proximal coaxial transmission line comprises:
   an inner conductor that extends from a distal end of the flexible coaxial cable, the inner conductor being electrically connected to a center conductor of the flexible coaxial cable;
   a proximal dielectric sleeve mounted around the inner conductor; and an outer conductor mounted around the proximal dielectric sleeve, wherein the distal needle tip comprises a distal dielectric sleeve mounted around the inner conductor, and wherein a distal portion of the outer conductor overlays a proximal portion of the distal dielectric sleeve.

7. The electrosurgical system according to claim 6, wherein the distal dielectric sleeve is made from a different material compared to the proximal dielectric sleeve.

8. The electrosurgical system according to claim 7, wherein a proximal end of the distal dielectric sleeve includes a protrusion disposed around the inner conductor, and wherein the protrusion is received in a complementarily shaped cavity at a distal end of the proximal dielectric sleeve.

9. The electrosurgical system according to claim 1, wherein the distal needle tip is configured to operate as a half wavelength transformer to deliver the microwave energy from the distal needle tip.

10. The electrosurgical system according to claim 1, further including a surgical scoping device having a flexible insertion cord for insertion into a patient's body, the flexible insertion cord having an instrument channel running along its length, and wherein the electrosurgical instrument is dimensioned to be received within the instrument channel.

11. An electrosurgical system for treating biological tissue, the electrosurgical system comprising:
   an electrosurgical generator configured to supply pulsed microwave energy; and
   an electrosurgical instrument comprising:
   a flexible coaxial cable arranged to convey the pulsed microwave energy; and
   a radiating tip portion connected at a distal end of the flexible coaxial cable and configured to receive the pulsed microwave energy, wherein the radiating tip portion has a maximum outer diameter that is 1.0 mm or less, and wherein the maximum outer diameter of the radiating tip portion is smaller than an outer diameter of the flexible coaxial cable, the radiating tip portion comprising:
a proximal coaxial transmission line for conveying the pulsed microwave energy; and
a distal needle tip mounted at a distal end of the proximal coaxial transmission line, the distal needle tip being arranged to deliver the pulsed microwave energy into biological tissue,
wherein the distal needle tip is configured to operate as a half wavelength transformer to deliver the microwave energy from the distal needle tip.

* * * * *